United States Patent
Strader et al.

(10) Patent No.: US 10,595,768 B2
(45) Date of Patent: Mar. 24, 2020

(54) PRICK TEST KIT

(71) Applicant: ROCA MEDICAL LTD., London (GB)

(72) Inventors: James Strader, Austin, TX (US); Jovan Hutton Pulitzer, Frisco, TX (US)

(73) Assignee: ROCA MEDICAL LTD., London (GB)

( * ) Notice: Subject to any disclaimer, the term of this patent is extended or adjusted under 35 U.S.C. 154(b) by 534 days.

(21) Appl. No.: 15/222,709

(22) Filed: Jul. 28, 2016

(65) Prior Publication Data
US 2017/0027494 A1   Feb. 2, 2017

Related U.S. Application Data

(60) Provisional application No. 62/198,072, filed on Jul. 28, 2015.

(51) Int. Cl.
*A61B 5/00*   (2006.01)
(52) U.S. Cl.
CPC .................................. *A61B 5/411* (2013.01)
(58) Field of Classification Search
CPC .................................................... A61B 5/411
See application file for complete search history.

(56) References Cited

U.S. PATENT DOCUMENTS

| | | | | |
|---|---|---|---|---|
| 5,104,620 A * | 4/1992 | Wiley | ..................... | A61B 5/411 422/430 |
| 5,671,753 A * | 9/1997 | Pitesky | ................ | A61B 17/205 600/556 |
| 5,931,794 A * | 8/1999 | Pitesky | ................... | A61B 5/411 600/556 |
| 6,488,937 B1 | 12/2002 | Smits | | |
| 6,684,916 B2 * | 2/2004 | Py | .............................. | A61J 1/18 141/2 |
| 2003/0082212 A1 | 5/2003 | Smits | | |
| 2006/0020514 A1 | 1/2006 | Yered | | |
| 2006/0212318 A1 | 9/2006 | Dooley et al. | | |

(Continued)

OTHER PUBLICATIONS

PCT: European Patent Office Searching Authority, International Search Report and Written Opinion of PCT/IB2015/001330 (related application), dated Oct. 5, 2015, 14 pgs, dated Oct. 5, 2015.

(Continued)

*Primary Examiner* — Daniel L Cerioni
*Assistant Examiner* — Yasmeen S Warsi

(57) ABSTRACT

A prick test kit comprises a bottom tray containing a plurality of wells disposed in an array, wherein each of the wells contains a vial of a small amount of a specific well associated antigen, with each well and associated vial having a different antigen disposed therein, each of the vials having a rubber cap disposed thereon that is sterile and able to be pricked by a needle such that the small amount of antigen can be removed therefrom. A penetrating plate is disposed above the wells and having on the lower surface thereof diametrically opposite from the vials in the wells a plurality of piercing needles, one associated with each of the wells and directed downward there to but not touching any of the files. A separating plate is disposed between the bottom tray and the penetrating plate. A sterile covering is provided for containing the entire assembly.

11 Claims, 5 Drawing Sheets

(56) References Cited

U.S. PATENT DOCUMENTS

2009/0169602 A1 7/2009 Senti et al.
2010/0203643 A1* 8/2010 Self .......................... B01L 9/06
436/47

OTHER PUBLICATIONS

Baumann L.S. et al., "Lip Silicone Granulomatous Foreign Body Reaction Treaded with Aldara (Imiquimod 5%)", Dermatologic Surgery Apr. 1, 2003 US, vol. 29, No. 4, Apr. 1, 2003 (Apr. 1, 2003), pp. 429-432, XP002745005, ISSN: 1076-0512, p. 429, left-hand column, paragraph middle. Apr. 1, 2003.
Prieto-Garcia Alicia et al: "Autoimmune Progesterone Dermatitis: Clinical Presentation and Management with Progesterone Desensitization for Successful In Vitro Fertilization", Fertility and Sterility, vol. 95, No. 3, Mar. 2011 (Mar. 2011), pp. 1121.e9-1121.e13, XP28147753, p. 1121.e9, left-hand column p. 1121.e12, left-hand column, paragraph top Mar. 1, 2001.
Cox et al., J. Allergy Clin. Immunol. 2011; 127(1 ):S1-S55 Jan. 1, 2011.
El Maghraby et al. Eur. J. Pharma. Sci. 2008; 34:203-222 Apr. 18, 2008.
PCT: European Patent Office Searching Authority, International Search Report and Written Opinion of PCT/IB2016/001332 (related application), dated Nov. 24, 2016, 13 pgs, dated Nov. 24, 2016.
E. Alvarez-Cuesta et al., "Subcutaneous immunotherapy", Allergy, vol. 61, No. s82, Oct. 2006 (Oct. 2006), pp. 5-13, XP055319495, UK Oct. 1, 2006.

* cited by examiner

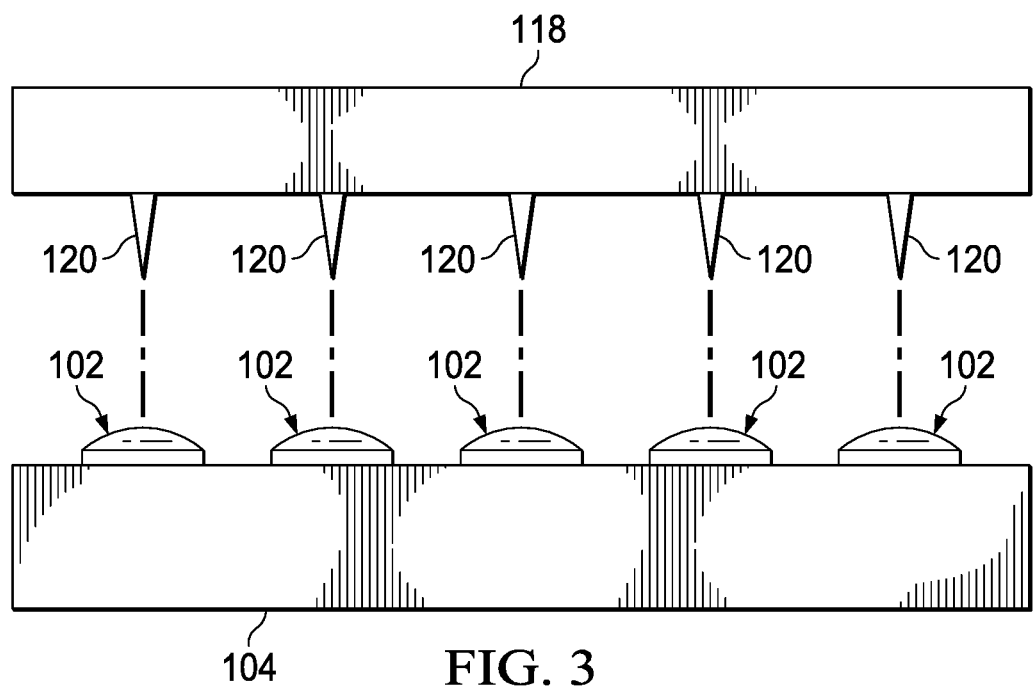
FIG. 3
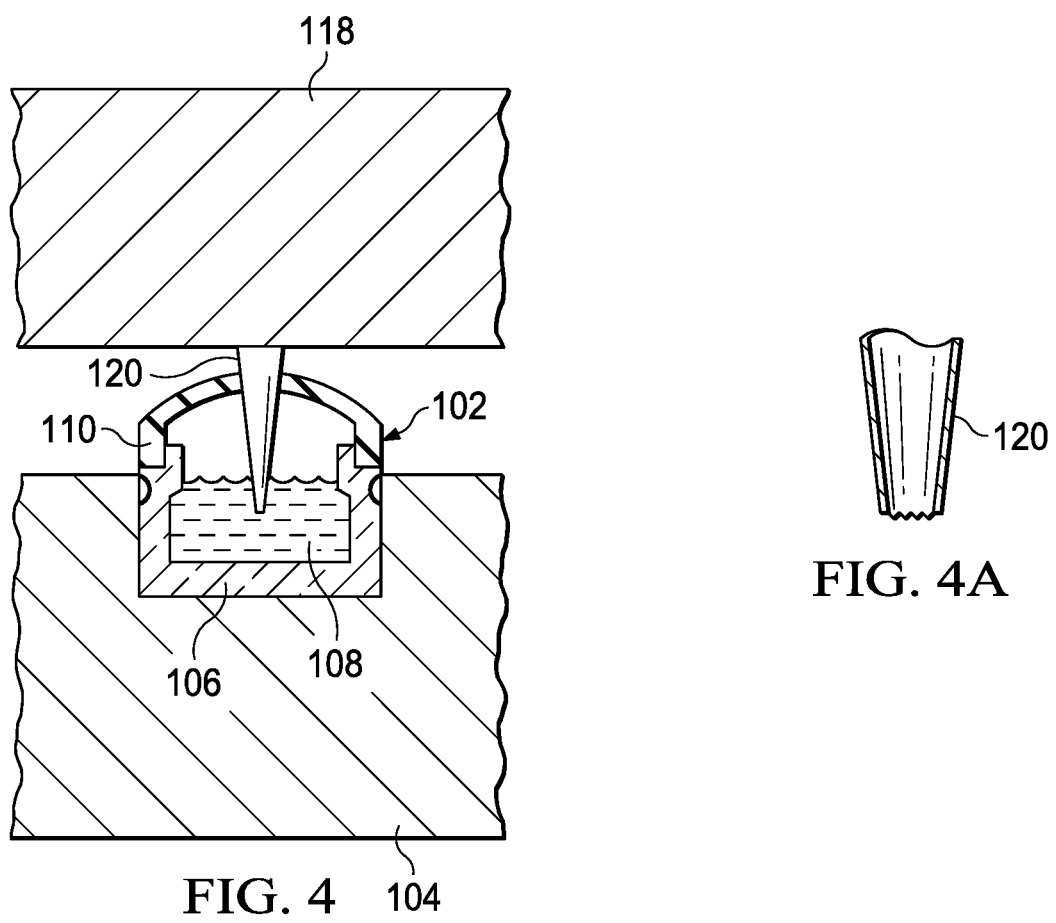
FIG. 4
FIG. 4A

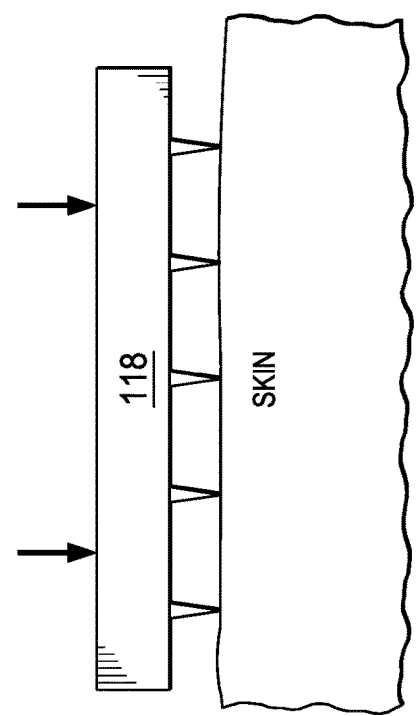
FIG. 6A
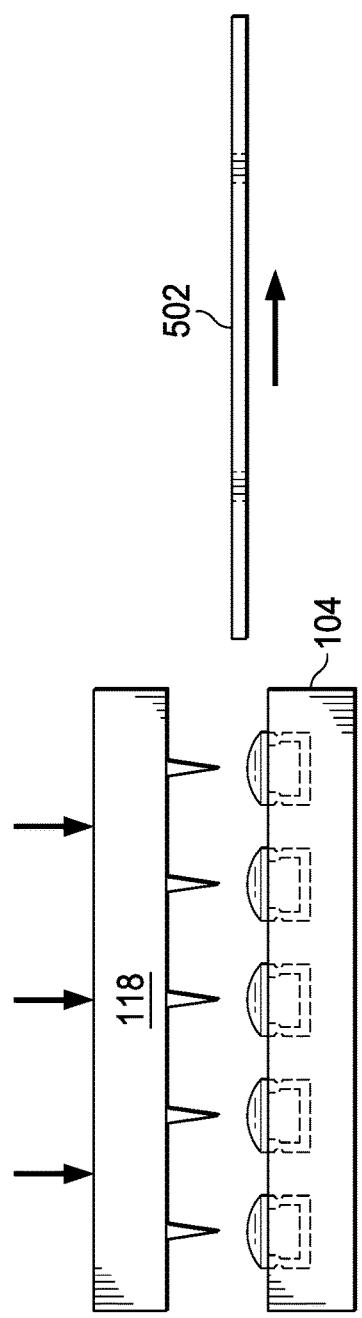
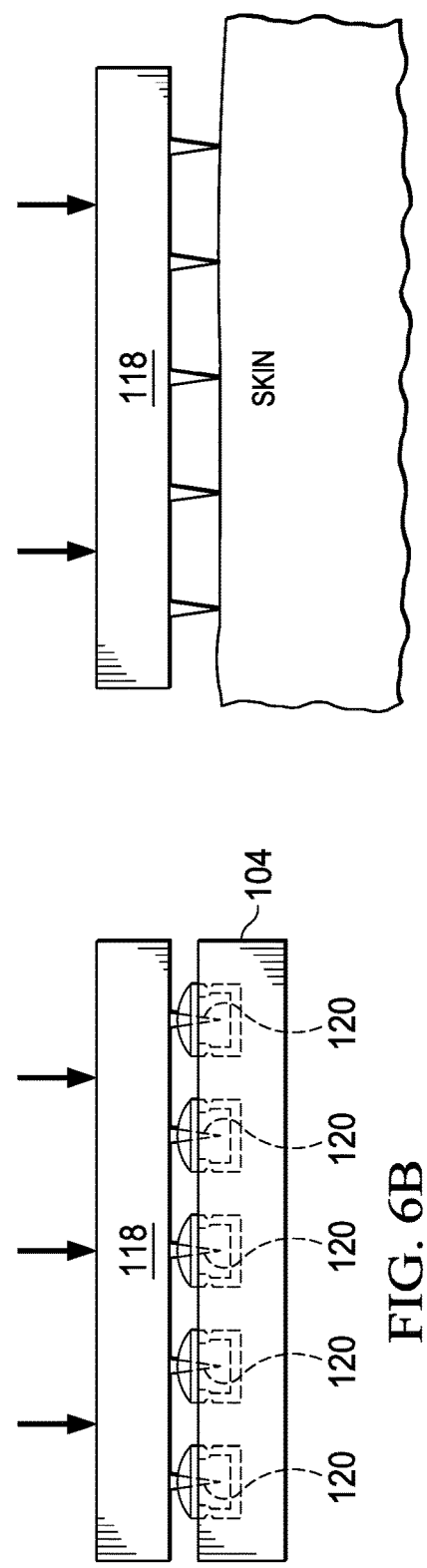
FIG. 6B
FIG. 6C
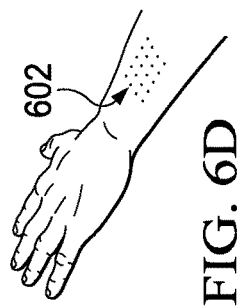
FIG. 6D

PRICK TEST KIT

CROSS-REFERENCE TO RELATED APPLICATIONS

This application claims the benefit of U.S. Provisional Application No. 62/198,072, filed on Jul. 28, 2015, entitled PRICK TEST KIT, which is herein incorporated by reference in its entirety.

TECHNICAL FIELD

The following disclosure relates to allergy testing and primarily, allergy testing with a prick test or skin testing.

BACKGROUND

Skin allergy testing is a method for medical diagnosis of allergies that attempts to provoke a small, controlled, allergic response. A microscopic amount of allergen is introduced to a patient skin by various means. One of these is a prick test wherein an allergen is introduced by pricking the skin with a needle containing a small amount of allergen. Other tests such as the skin scratch test provides for a deep dermic scratch with the help of a blunt bottom of a lancet, and intra-dermic test involving a tiny quantity of allergen injected under the dermis with a hypodermic syringe, a skin scraped test involving a superficial scrape performed with the help of the bevel of a needle to remove the superficial layer of the epidermis and a patch test wherein a patch is applied to the skin, the patch containing a small amount of allergen.

In the prick test, a few drops of purified allergen are generally pricked onto the skin surface, usually the forearm. This test is usually done in order to identify allergies caused by such things as pet dander, dust, pollen, foods or dust mites. The skin prick test involves first placing a small amount of substances that may be causing your symptoms on the skin, most often on the forearm or upper arm back. Some of the prick test kits that are available are utilized to stretch the amount of antigen that can be utilized. Typically, a 5 mL bottle of antigen can provide up to 1800 test of glycerinated extract. Typically, there are provided a plurality of wells in a tray, with each well being filled with 0.125 mL of extract. A pick is utilized to dip the end thereof into the small amount of extract disposed in the bottom of the well and then a particular site is pricked on an individual. Some of these picks provide for multiple well associations, such that a series of six or seven wells in a line in the tray can be accessed such that six different antigens can be applied to an individual's skin at a single time. There are even larger arrays of picks that can be dipped into the well for treating a large area with more antigens at the same time. One of the issues is that the antigen must be removed from a sterile bottle with a needle or the such, since the sterile bottle containing the antigen typically has some type of rubber stopper through which the hypodermic needle can be inserted. Once the hyperbaric needle is inserted therein, the sterile barrier is broken. The antigen is indisposed into the well and then the pick disposed therein multiple times. There is not necessarily any sterilization procedure between applying this to the skin of an individual and then disposing the pick back into the well for sealing that well. Thus, once the antigen is extracted from the 5 mL bottle, the first use of the antigen is the only sterile use. Thereafter, application thereof up to 1800 times can potentially result in issues.

SUMMARY

In one embodiment, a prick test kit for delivering antigens is provided. The prick test kit comprises a bottom tray containing a plurality of wells disposed in an array, wherein each of the wells contains a vial of a small amount of a specific well associated antigen, with each well and associated vial having a different antigen disposed therein, each of the vials having a rubber cap disposed thereon that is sterile and able to be pricked by a needle such that the small amount of antigen can be removed therefrom. A penetrating plate is disposed above the wells and having on the lower surface thereof diametrically opposite from the vials in the wells a plurality of piercing needles, one associated with each of the wells and directed downward there to but not touching any of the files. A separating plate is disposed between the bottom tray and the penetrating plate. A sterile covering is provided for containing the entire assembly.

BRIEF DESCRIPTION OF THE DRAWINGS

For a more complete understanding, reference is now made to the following description taken in conjunction with the accompanying Drawings in which:

FIG. 3 illustrates a diagrammatic view of the arrangement of a top plate with prick needles in alignment with a plurality of vials;

FIG. 4 illustrates a cross-sectional view of a vial penetrated by a needle;

FIG. 4A illustrates a cross-sectional view of a piercing needle;

FIGS. 6A-D illustrate the operation of the overall device for applying indigents to the skin.

DETAILED DESCRIPTION

Figure 1:
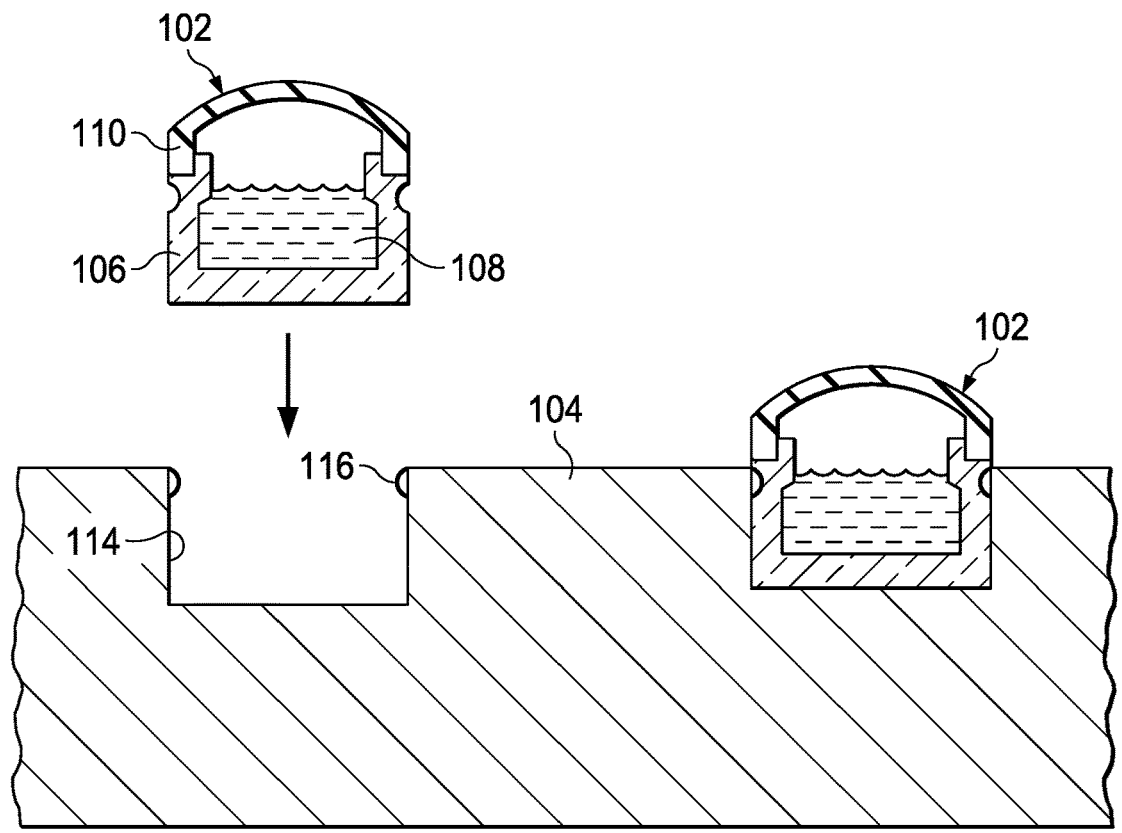
FIG. 1 illustrates a cross-sectional view of a small vial disposed in a receptacle tray.

Referring now to FIG. 1, there is illustrated a cross-sectional view of two vials 102 disposed in a carrier tray 104. Each of the vials is comprised of a 1 mL glass container 106 which has disposed therein 1 mL of glycerated extract 108. A rubber stopper 110 is disposed over the surface thereof, this rubber stopper 110 allowing a hypodermic needle to be disposed therethrough. The vial 102 is disposed within a receptacle 114 on the tray 104. There is typically a spring-loaded tab 116 at the upper edge of the receptacle 114 for each of the vials 102 to maintain the vial 102 in a secure position.

Figure 2:
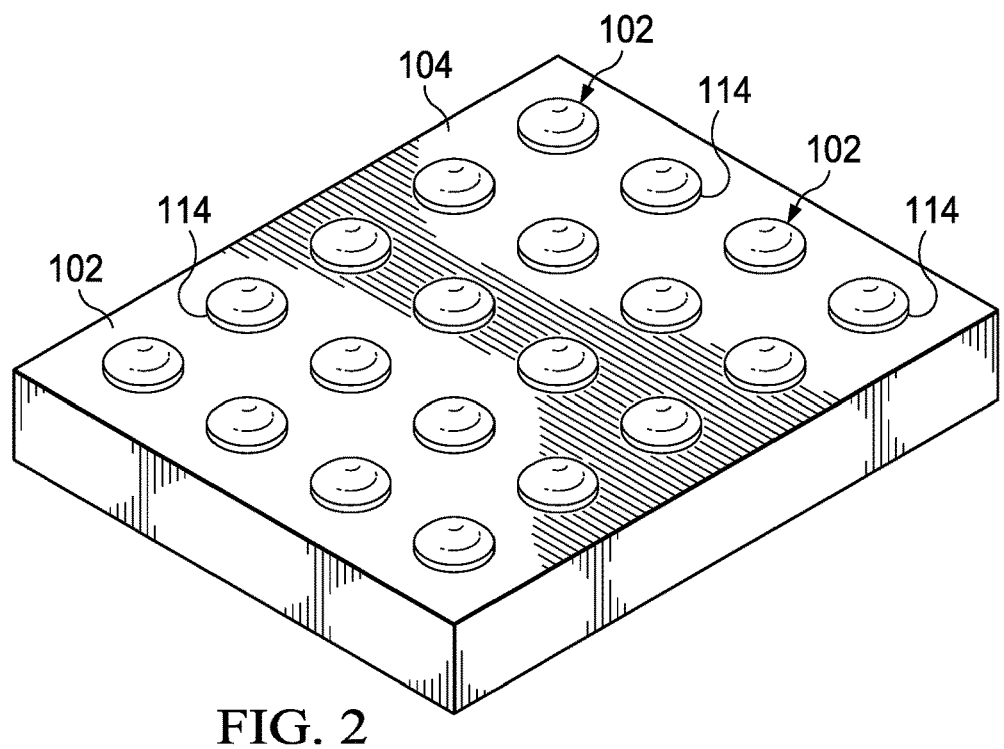
FIG. 2 illustrates a perspective view of a tray with vials disposed therein and arranged in an array.

Referring now to FIG. 2, there is illustrated a perspective view of the tray 114 with an array of vials 102 disposed therein. Each of these vials 102 has contained therein 1 mL of a particular antigen, typically each vial 102 having a different antigen disposed therein.

Referring now to FIG. 3, there is illustrated a side view of the operation of a top plate 118, referred to as a piercing plate 118 that has a plurality of piercing needles 120 which function as the facilitator of the prick test, these being disposed on a lower surface of the piercing plate 118. They are aligned each with an associated vial 102. Thus, the piercing plate 118 would have an array of piercing needles 120 disposed thereon which correspond to the arrays of vials 102.

Referring now to FIG. 4, there is illustrated a cross-sectional view of a vial 102 pierced by the piercing needle 120. It can be seen that, once the piercing needle pierces the stopper 110, it will have a small amount of the 1 mL of antigen disposed thereon. A detail of the tip of the piercing needle 120 is illustrated in FIG. 4A. This shows a serrated edge that allows a larger surface area for taking up more antigen. However, the 1 mL of antigen is a one-use-one-patient-only amount.

Figure 5:
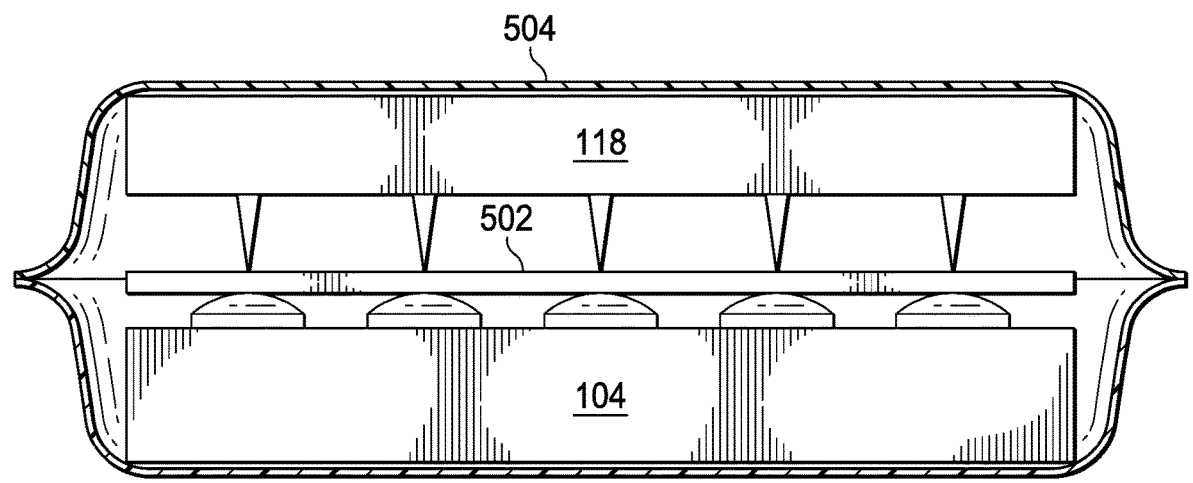
FIG. 5 illustrates a side view of a packaged and sterile prick test device in accordance with the present disclosure.

Referring now to the FIG. 5, there is illustrated a side view of a packaged prick test device. It can be seen that the piercing layer 118 is separated from the tray 104 by a removable layer 52. This removable layer 502 can be made of a relatively impenetrable material such as mylar or some material that can be sterilized. This layer protects the needles 118 from penetrating the upper ends of the vials 102. An outer shrinkwrap layer 504 is provided over the entire device to provide a sterile environment.

Referring now to FIGS. 6A-D, there are illustrated diagrammatic views for the operation of the device. In FIG. 6A, the layer 502 is extracted from between the piercing layer 118 and tray 104. In the next figure, FIG. 6B, the piercing layer 118 is pressed down onto the tray 104 such that the piercing needles 120 pierced the cap 110 for each of the associated vials 102. This allows the tip of the piercing needles 120 to be inserted into a particular and associated antigen in that particular and associated vial 102. In FIG. 6C, piercing layer 118 is then pressed against the skin of the individual such that the small amount of antigen on the tip of the piercing needle 120 can be disposed beneath the dermis of this individual. FIG. 6D illustrates the pattern that is formed on this again, this being a pattern 602. Since the antigens are prepackaged and pre-labeled, all that is necessary is to determine the orientation of the array of piercing needles on the piercing layer 118 in order to determine which antigen is associated with which particular prick site.

Figure 7A:
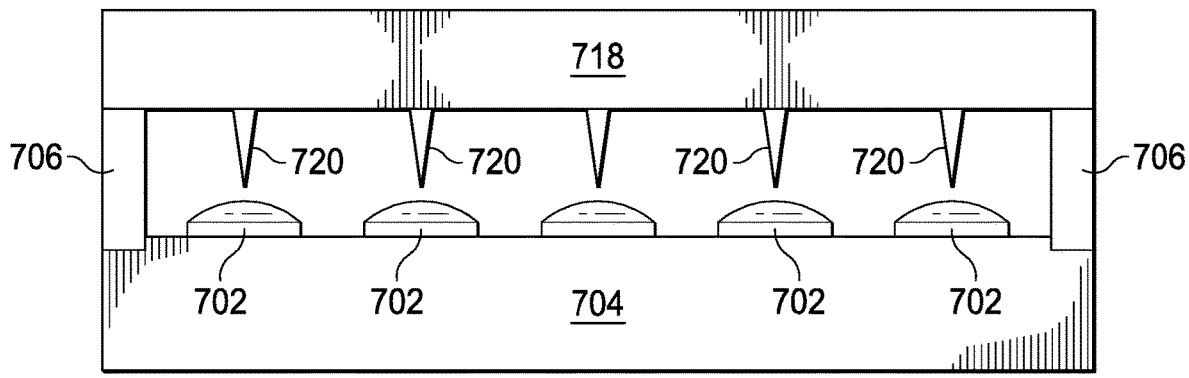
FIGS. 7A-D illustrate diagrammatic views of another embodiment of the device that includes a plurality of tabs disposed between a top tray and a carrier tray.
Figure 7B:
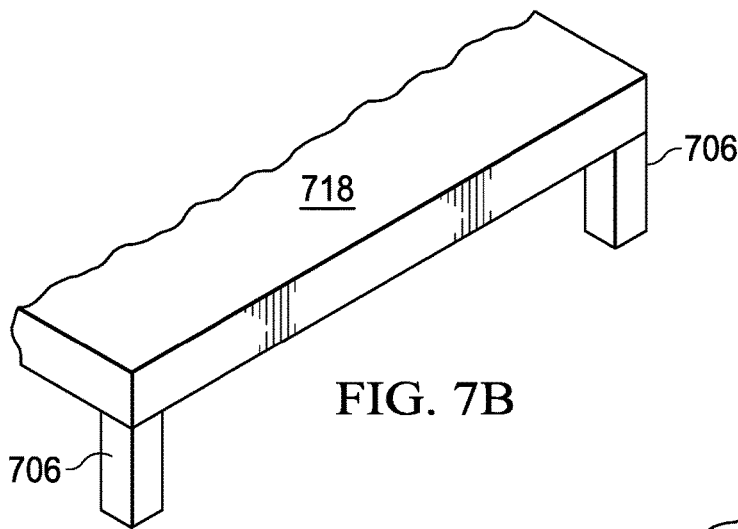

Referring now to FIGS. 7A-D, there are illustrated diagrammatic views of another embodiment of the device. In FIG. 7A, there is illustrated a side view of the operation of a top plate 718, referred to as a piercing plate 718 that has a plurality of piercing needles 720 which function as the facilitator of the prick test, these being disposed on a lower surface of the piercing plate 718. They are aligned each with an associated vial 702 positioned in a carrier tray 704. Thus, the piercing plate 718 would have an array of piercing needles 720 disposed thereon which correspond to the arrays of vials 702. This embodiment further includes a plurality of tabs 706. The plurality of tabs 706 are attached to the top plate 718, preferably at each corner of the top plate 718, and disposed downward such that they contact the carrier tray 704 when the top plate 718 is placed over the carrier tray 704. FIG. 7B further illustrates the plurality of tabs 706 extending down from the top plate 718.

Figure 7C:
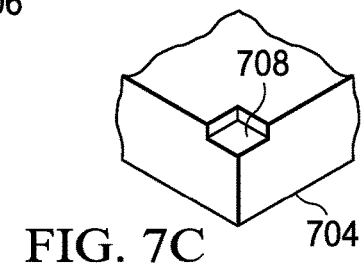

FIG. 7C illustrates that the carrier tray 704 includes a recessed portion 708. The recessed portion 708 serves to allow the plurality of tabs 706 to sit within the recessed portion, adding further stability so that the top plate 718 does not slide in any direction from the carrier tray 704 and to maintain the piercing needles 720 away from the rubber caps by a predetermined distance for shipping and storage. As such, the carrier tray 704 may have as many recessed portions as needed to allow for each of the plurality of tabs 706 to sit within a recessed portion of the carrier tray 704.

Figure 7D:
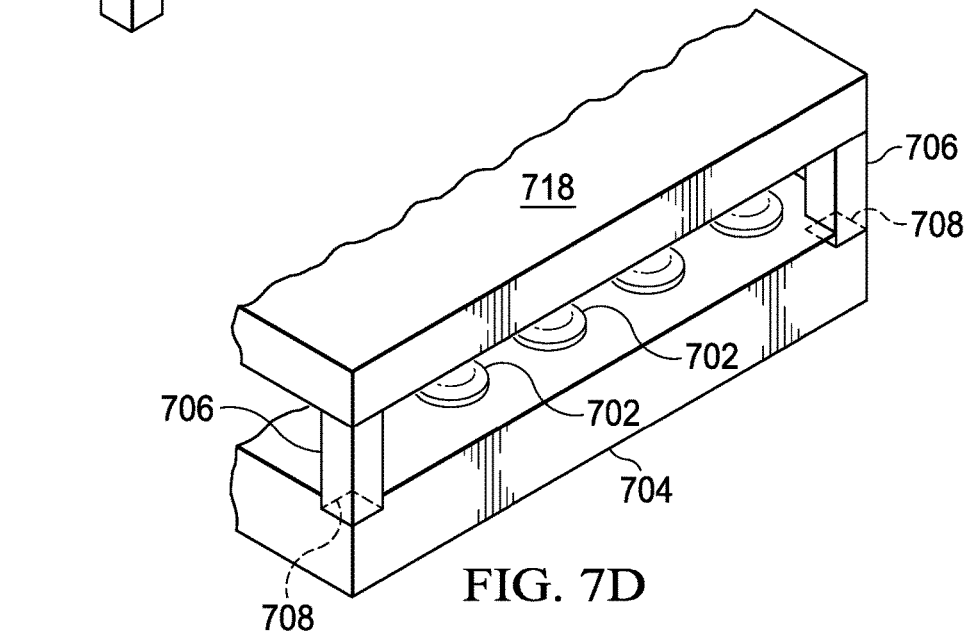

FIG. 7D illustrates one of the plurality of tabs 706 sitting within a recessed portion 708, with a dotted line indicating that the tab is sitting within the recessed portion 708 of the carrier tray 704. The plurality of tabs 706 prevent the top plate 718 from being pressed against the carrier tray and to maintain the needles 720 from contacting and piercing the vials through the rubber cap. This prevents the vials 702 or the needles 720 from being damaged during shipment, such as from pressure or weight being applied to the top of the device. Once the device is received, the plurality of tabs 706 may be removed via a perforated edge or other means of removing the plurality of tabs 706. The plurality of tabs 706 may be made of any material that is strong enough to prevent contact between the top plate 718 and the carrier tray 704, while still allowing for the plurality of tabs 706 to be removed, such as plastic. Additionally, although not shown, there may also be a removable layer, such as that described herein with respect to reference number 502, included and disposed between the top plate 718 and the carrier tray 704.

Although the preferred embodiment has been described in detail, it should be understood that various changes, substitutions and alterations can be made therein without departing from the spirit and scope of the invention as defined by the appended claims.

What is claimed is:

1. A prick test kit, comprising:
   a bottom tray containing a plurality of wells disposed in an array, wherein each of the plurality of wells contains a vial of a small amount of a specific well-associated antigen, with each well and associated vial having a different antigen disposed therein, and wherein each of the plurality of wells includes a plurality of spring-loaded tabs disposed at an upper edge of the well, wherein each one of the plurality of spring-loaded tabs is operable to cooperate with one of a plurality of notched portions of the associated vial, to maintain the vials in the plurality of wells; and
   a penetrating plate disposed above the plurality of wells and having on a lower surface thereof diametrically opposite from the vials in the wells a plurality of piercing needles, one associated with each of the plurality of wells and directed downward thereto but not touching any of the vials.

2. The prick test kit of claim 1, wherein each of the vials has a rubber cap disposed thereon, wherein the rubber cap is sterile and is able to be pricked by a needle such that the small amount of antigen can be removed therefrom.

3. The prick test kit of claim 2, further comprising a separating plate disposed between the bottom tray and the penetrating plate.

4. The prick test kit of claim 2, further comprising a sterile covering for containing the entire prick test kit.

5. The prick test kit of claim 4, further comprising a separating plate disposed between the bottom tray and the penetrating plate.

6. The prick test kit of claim 1, wherein the penetrating plate includes a plurality of tabs directed downward towards the bottom tray.

7. The prick test kit of claim 6, wherein the bottom tray includes a plurality of recessed portions, with the number of the plurality of recessed portions corresponding to the number of the plurality of tabs, such that the plurality of tabs may rest within the plurality of recessed portions.

8. The prick test kit of claim 1, wherein each of the plurality of piercing needles has a serrated edge.

9. A method for using a prick test kit, comprising:
removing a separating plate from between a bottom tray and a penetrating plate,
  wherein the bottom tray contains a plurality of wells disposed in an array, with each of the plurality of wells containing a vial of a small amount of a well-associated antigen,
  wherein the penetrating plate is disposed above the plurality of wells and having on a lower surface thereof diametrically opposite from the vials in the wells a plurality of piercing needles, one associated with each of the plurality of wells and directed downward thereto but not touching any of the vials, and
  wherein each of the plurality of wells includes a plurality of spring-loaded tabs disposed at an upper edge of the well, wherein each one of the plurality of spring-loaded tabs is operable to cooperate with one of a plurality of notched portions of the vial, to maintain the vials in the plurality of wells;
  pressing the penetrating plate down onto the bottom tray such that the plurality of piercing needles pierce a sterile rubber cap disposed on each of the vials such that the plurality of piercing needles enters the vials and comes into contact with the small amount of antigen disposed in the vials;
  removing the small amount of antigen via each of the plurality of piercing needles; and
  pressing the plurality of piercing needles against the skin of a patient, such that the small amount of antigen is transferred beneath the dermis of the patient.

10. The method of claim 9, further comprising removing a plurality of tabs from the penetrating plate, wherein the plurality of tabs served to separate the penetrating plate and the bottom tray during shipment and before removal, and wherein the plurality of tabs sat in recessed portions of the bottom tray before removal.

11. The method of claim 9, further comprising removing a sterile covering containing the entire prick test kit.

* * * * *